United States Patent
Brisken

[19]

[11] Patent Number: 5,931,805
[45] Date of Patent: Aug. 3, 1999

[54] CATHETERS COMPRISING BENDING TRANSDUCERS AND METHODS FOR THEIR USE

[75] Inventor: Axel F. Brisken, Fremont, Calif.

[73] Assignee: Pharmasonics, Inc., Sunnyvale, Calif.

[21] Appl. No.: 08/867,007

[22] Filed: Jun. 2, 1997

[51] Int. Cl.⁶ .................................................. A61B 17/20
[52] U.S. Cl. ............................................................ 604/22
[58] Field of Search ...................... 604/19, 22; 600/437, 600/466, 471; 606/167, 169

[56] References Cited

U.S. PATENT DOCUMENTS

| | | |
|---|---|---|
| 3,433,226 | 3/1969 | Boyd . |
| 3,565,062 | 2/1971 | Kuris . |
| 4,692,139 | 9/1987 | Stiles . |
| 4,698,058 | 10/1987 | Greenfield et al. . |
| 4,808,153 | 2/1989 | Parisi . |
| 4,841,977 | 6/1989 | Griffith et al. . |
| 4,870,953 | 10/1989 | Michael et al. . |
| 4,936,281 | 6/1990 | Stasz . |
| 4,948,587 | 8/1990 | Kost et al. . |
| 5,053,044 | 10/1991 | Mueller et al. . |
| 5,069,664 | 12/1991 | Guess et al. ............................. 604/22 |
| 5,085,662 | 2/1992 | Willard . |
| 5,109,861 | 5/1992 | Walinsky et al. . |
| 5,117,831 | 6/1992 | Jang et al. . |
| 5,163,421 | 11/1992 | Bernstein et al. . |
| 5,181,920 | 1/1993 | Mueller et al. . |
| 5,197,946 | 3/1993 | Tachibana . |
| 5,240,004 | 8/1993 | Walinsky et al . |
| 5,267,954 | 12/1993 | Nita . |
| 5,267,985 | 12/1993 | Shimada et al. . |
| 5,269,297 | 12/1993 | Weng et al. . |
| 5,276,546 | 1/1994 | Mische et al. . |
| 5,282,785 | 2/1994 | Shapland et al. . |
| 5,286,254 | 2/1994 | Shapland et al. . |
| 5,304,115 | 4/1994 | Pflueger et al. . |
| 5,315,998 | 5/1994 | Tachibana et al. . |
| 5,318,014 | 6/1994 | Carter . |

(List continued on next page.)

FOREIGN PATENT DOCUMENTS

| | | |
|---|---|---|
| 0189329A2 | 7/1989 | European Pat. Off. . |
| 3-63041 | 3/1991 | Japan . |
| WO 90/01300 | 2/1990 | WIPO . |
| WO 91/19529 | 12/1991 | WIPO . |
| WO 94/05361 | 3/1994 | WIPO . |
| WO 95/22284 | 8/1995 | WIPO . |
| WO 95/24159 | 9/1995 | WIPO . |

OTHER PUBLICATIONS

Tachibana, M.D., Katsuro, "Enhancement of Fibrinolysis with Ultrasound Energy," *JVIR*, vol. 3, No. 2, 1992, pp. 299–303.

Yumita et al. "Synergistic Effect of Ultrasound and Hematoporphyrin on Sarcoma 180," *Jpn. J. Cancer Res.*, vol. 81, 1990, pp. 304–308.

Rosenschein, M.D., Uri et al. "Experimental Ultrasonic Angioplasty: Disruption of Atherosclerotic Plaques and Thrombi in Vitro and Arterial Recanalization in Vivo," *JACC*, vol. 15, No. 3, Mar. 1, 1990, pp. 711–717.

*Primary Examiner*—Wynn Wood Coggins
*Assistant Examiner*—Michael J. Hayes
*Attorney, Agent, or Firm*—Townsend&Townsend&Crew LLP

[57] ABSTRACT

A catheter comprises a catheter body having a bending plate transducer disposed at or near its distal end. The bending plate transducer is typically a unimorph, bimorph, or other conventional vibratory transducer capable of imparting pressure waves in a direction generally normal to the plane of the transducer. The bending plate transducers may be disposed at a distal end of the catheter body, for example, as a cantilever beam, or may alternately be disposed within the catheter body. The catheters may further comprise lumens for drug delivery, balloons for encircling the transducer structures, or the like. The catheters are useful in a variety of lumenal therapeutic procedures, including drug delivery, stenotic disruption within blood vessel, and the like.

26 Claims, 4 Drawing Sheets

U.S. PATENT DOCUMENTS

| | | |
|---|---|---|
| 5,324,255 | 6/1994 | Passafaro et al. . |
| 5,342,292 | 8/1994 | Nita et al. . |
| 5,344,395 | 9/1994 | Whalen et al. . |
| 5,362,309 | 11/1994 | Carter . |
| 5,380,273 | 1/1995 | Dubrul et al. . |
| 5,397,301 | 3/1995 | Pflueger et al. . |
| 5,447,509 | 9/1995 | Mills et al. . |
| 5,456,259 | 10/1995 | Barlow et al. . |
| 5,458,568 | 10/1995 | Racchini et al. . |
| 5,458,631 | 10/1995 | Xavier . |
| 5,462,523 | 10/1995 | Samson et al. . |
| 5,465,725 | 11/1995 | Seyed-Bolorforosh . |
| 5,474,530 | 12/1995 | Passafaro et al. . |
| 5,474,531 | 12/1995 | Carter . |
| 5,735,811 | 4/1998 | Brisken .................................. 604/22 |

CATHETERS COMPRISING BENDING TRANSDUCERS AND METHODS FOR THEIR USE

BACKGROUND OF THE INVENTION

1. Field of the Invention

The present invention relates generally to medical devices and methods. More particularly, the present invention relates to apparatus and methods for performing intralumenal procedures using catheters having ultrasonically oscillated surfaces which can impart energy to a blood vessel or other body lumen being treated.

Despite the growing sophistication of medical technology, vascular (blood vessel) diseases, such as acute myocardial infarction (heart attack) and peripheral arterial thrombosis (blood clots in leg arteries), remain a frequent, costly, and very serious problem in health care. Current methods of treatment, often expensive, are not always effective. In the U.S. alone, the cost of treatment and support and the loss of productivity due to vascular diseases together exceed $40 billion per year.

The core of the problem is that diseased sites within the blood vessels narrow and eventually become completely blocked as a result of the deposition of fatty materials, cellular debris, calcium, and/or blood clots, thereby blocking the vital flow of blood. Current treatments include drugs, interventional devices, and/or bypass surgery. High doses of thrombolytics (clot-dissolving drugs) are frequently used in an effort to dissolve the blood clots. Even with such aggressive therapy, thrombolytics fail to restore blood flow in the affected vessel in about 30% of patients. In addition, these drugs can also dissolve beneficial clots or injure healthy tissue causing potentially fatal bleeding complications.

While a variety of interventional devices are available, including angioplasty, atherectomy, and laser ablation catheters, the use of such devices to remove obstructing deposits may leave behind a wound that heals by forming a scar. The scar itself may eventually become a serious obstruction in the blood vessel (a process known as restenosis). Also, diseased blood vessels being treated with interventional devices sometimes develop vasoconstriction (elastic recoil), a process by which spasms or abrupt reclosures of the vessel occur, thereby restricting the flow of blood and necessitating further intervention. Approximately 40% of treated patients require additional treatment for restenosis resulting from scar formation occurring over a relatively long period, typically 4 to 12 months, while approximately 1-in-20 patients require treatment for vasoconstriction, which typically occurs from 4 to 72 hours after the initial treatment.

The use of ultrasonic energy has been proposed both to mechanically disrupt clot and to enhance the intravascular delivery of drugs to dissolve clot and inhibit restenosis. Ultrasonic energy may be delivered intravascularly using specialized catheters having an ultrasonically vibrating surface at or near their distal ends.

It would be desirable to provide improved devices, systems and methods for treating vascular and other lumenal diseases, particularly stenotic diseases which occlude the coronary and other arteries. In particular, it would be desirable to provide novel ultrasonic catheter configurations capable of transferring energy into body lumens in a variety of ways. Such catheter configurations should be compatible with conventional catheter designs, such as angioplasty catheters, drug delivery catheters, perfusion catheters, and atherectomy catheters, but should also be useful as stand-alone devices intended to disrupt clot in blood vessels and perform other procedures in different body lumens. At least some of these objectives will be met by the catheter designs described and claimed hereinafter.

2. Description of the Background Art

Catheters having ultrasonic elements with the capability of delivering thrombolytic and other liquid agents are described in U.S. Pat. Nos. 5,362,309; 5,318,014; 5,315,998; 5,197,946; 5,380,273; 5,344,395; 5,342,292; 5,324,255; 5,269,297; 5,267,954; 4,808,153; 4,692,139; and 3,565,062; in WO 90/01300; and in Tachibana (1992) JVIR 3:299–303. See, in particular, FIGS. 6A and 6B of U.S. Pat. No. 5,197,946, which disclose a cantilevered transducer designed for non-bending actuation. A catheter system having a pair of spaced-apart balloons with a coiled piezoelectric strip therebetween is described in U.S. Pat. No. 5,279,546. Catheters having elongate ultrasonic transmission elements and inflatable cuffs are described in U.S. Pat. Nos. 5,397,301; 5,304,115; and 4,870,953. A tunneling catheter having a radiofrequency, laser, or ultrasonic active distal end disposed within an angioplasty catheter is described in EP 189 329. An atherectomy catheter having an ultrasonically enhanced blade disposed adjacent an asymmetrically mounted balloon is described in U.S. Pat. No. 5,085,662. Phonophoresis transducers disposed within porous, inflatable balloons are suggested in U.S. Pat. Nos. 5,286,254 and 5,282,785. A rigid ultrasonic probe intended for treating vascular plaque and having fluid delivery means is described in U.S. Pat. No. 3,433,226. An ultrasonic transmission wire intended for intravascular treatment is described in U.S. Pat. No. 5,163,421 and Rosenschein et al. (1990) *JACC* 15:711–717. Ultrasonic enhancement of systemic and localized drug delivery is described in U.S. Pat. Nos. 5,267,985; and 4,948,587; in WO 94/05361 and WO 91/19529; in JP 3-63041; and Yumita et al. (1990) *Jpn. J. Cancer Res.* 81:304–308. An electrosurgical angioplasty catheter having ultrasonic enhancement is described in U.S. Pat. No. 4,936,281. An infusion and drainage catheter having an ultrasonic cleaning mechanism is described in U.S. Pat. No. 4,698,058. Angioplasty balloon catheters having axial blade atherectomy, ultrasonic imaging, and rotary blade atherectomy devices at their distal ends are described in U.S. Pat. Nos. 5,053,044; 5,117,831; and 5,181,920, respectively.

The present application is related to copending applications assigned to the assignee of the present application having the following serial numbers: Ser. No. 08/565,575 (now U.S. Pat. No. 5,725,494); Ser. No. 08/566,740(now U.S. Pat. No. 5,728,062); Ser. No. 08/566,739(now U.S. Pat. No. 5,735,811); and Ser. No. 08/708,589(now U.S. Pat. No. 5,846,218).

The full disclosures of each of the above listed U.S. patents and copending applications are hereby incorporated herein by reference.

SUMMARY OF THE INVENTION

According to the present invention, improved devices and methods are provided for the delivery of vibrational energy to body lumens, such as blood vessels. The devices are usually catheters useful for the primary or ancillary treatment of lumenal diseases, such as vascular occlusive diseases. Such treatment can be in the form of the delivery of vibrational energy for the primary disruption of clot or plaque at a stenosed region within the blood vessel. The treatment may also comprise the delivery of vibrational energy to enhance the intramural penetration or activity of drugs which are delivered to a diseased region of the body lumen. Both the disruption of stenotic material and the delivery of drugs can be performed in combination with other primary treatments, such as angioplasty, atherectomy, laser ablation, stent delivery, and the like.

The catheters of the present invention will comprise a catheter body having a proximal end and a distal end. A bending plate transducer is attached to or within the catheter body near the distal end thereof. The transducer is arranged to vibrationally flex about an axis within a plane of the transducer. The resulting vibrational energy, which is usually in the sonic to low ultrasonic range, will be transferred to the fluid environment surrounding the distal end of the catheter, into stenotic materials or structures within the lumen itself, and/or directly into the lumenal wall in order to effect a desired therapeutic modality. The frequency of operation will typically be in the range from 1 kHz to 40 kHz, usually from 2 kHz to 30 kHz. The vibrational amplitude will typically be in the range from 150 μm to 500 μm, when the system is unloaded. When the catheter is present in its normal lumenal environment, i.e. surrounded by a natural body fluid, such as blood and/or by an introduced fluid, such as saline optionally carrying a drug, the vibrational amplitude will usually be at least 5 μm, typically being damped to the range from 5 μm to 50 μm, more usually from 10 μm to 30 μm.

In a first specific embodiment, the catheter of the present invention will comprise a vibrational transducer which projects distally from the distal end of the catheter body, i.e. is arranged as a cantilever beam from the distal end of the catheter body. The vibrational transducer will thus be arranged to oscillate in a lateral or transverse motion so that pressure waves are imparted in opposite lateral directions from the two surfaces of the transducer. Such a configuration is particularly suited for introducing energy into drug solutions which are delivered, typically by the same catheter, to a treatment region. The configurations are also suitable for directly imparting energy into clot or other stenotic material within the blood vessels and/or into the blood vessel wall for a variety of purposes. In a preferred aspect of this configuration, one or more drug delivery lumens will be provided in the catheter body to release a drug in the vicinity of the transducer.

In a second specific embodiment, the catheter of the present invention will comprise one or more vibrational transducers embedded within the catheter body, typically near the distal end, more typically within 0 cm to 5 cm of the distal end, preferably within 0 cm to 1 cm of the distal end. The vibrational transducers may be arranged in pairs, in groups of three, in groups of four, or in higher numbers, typically being symmetrically arranged about the cross-section of the catheter. Such catheter configurations are suitable for enhancing drug delivery and may also be combined with or within balloon structures on the catheter to delivery energy into a lumenal wall through the balloon. That is, the inflation medium within the balloon may be used to couple vibrational energy from the transducers directly into the lumenal wall.

In yet another specific embodiment, the catheter of the present invention will comprise one or more annular disks which are disposed transversely relative to the axis of the catheter body. The annular disks will thus vibrate generally in an axial direction and will induce pressure waves which travel axially. Such catheter configurations are also useful for imparting energy into drug solutions which have been introduced to the treatment site, usually using the same catheter. Annular disk configurations may be employed between axially spaced-apart balloons (e.g. as described in co-pending application Ser. No. 08/566,739) and/or within porous drug delivery balloons.

The bending plate transducers used in any of the catheter configurations described above may comprise conventional transducer structures, typically including at least one active layer which oscillates axially when energized by an appropriate driving force, typically an alternating current at the desired frequency of operation. The active layer will be combined with an opposed layer, which may be an inactive layer (e.g. a metal plate which does not oscillate) or may be another active layer (e.g. another layer which oscillates in phase or out-of-phase with the first active layer). In all cases, the active layers will typically be piezoelectric materials which are energized via electrodes formed on opposed surfaces thereof. Specific transducer designs will be discussed in detail below.

According to the method of the present invention, a catheter having a bending plate transducer is positioned within a body lumen so that the transducer lies adjacent to a target site therein. The transducer is energized to vibrationally flex about an axis within a plane of the transducer in order to impart energy into a fluid environment within the body lumen, to stenotic material occluding or partially occluding the lumen, and/or directly into the lumenal wall. Thus, the catheter may be positioned so that the transducer vibrates freely within the fluid environment, or may be positioned against an occluding structure and/or the lumenal wall. The transducer will be operated at a frequency and, at an amplitude within the ranges set forth above. The body lumen is preferably a blood vessel, and the target site is usually a stenosed region. The stenosed region may have been previously treated by angioplasty, atherectomy, or other conventional procedure, or may be concurrently so treated. The method may further comprise releasing a therapeutic agent into the lumen, either prior to energizing the transducer or while the transducer is energized. In some cases, it may be desirable to inflate a balloon around the transducer, wherein the balloon inflation medium can act to couple the vibrational energy of the catheter into the lumenal wall.

DESCRIPTION OF THE SPECIFIC EMBODIMENTS

Figure 1:
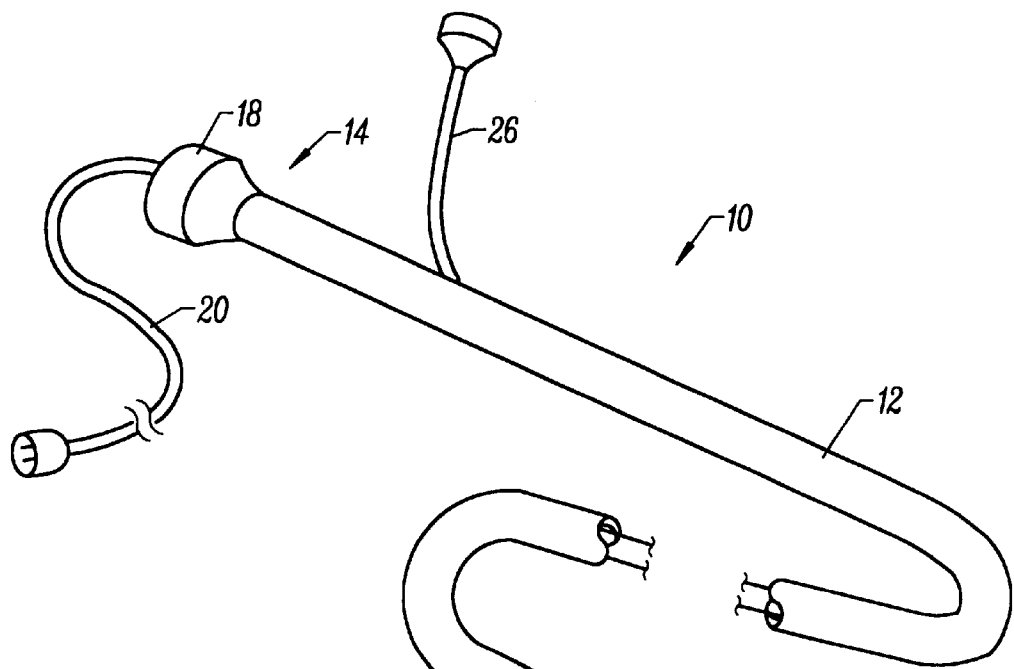
FIG. 1 is an isometric view of a catheter constructed in accordance with the principles of the present invention, having a bending plate transducer projecting distally from a distal end thereof.

The present invention provides apparatus and methods for the treatment of lumenal conditions, particularly for the treatment of diseases of the coronary and peripheral vasculature. Specific conditions include coronary and peripheral arterial disease and thrombosis. The apparatus and methods are useful for primary treatment of such diseases, where the purpose is to ablate, dissolve, or otherwise disrupt the clot, plaque, or other stenotic lesions which are responsible for the disease. For example, catheters constructed according to the principles of the present invention can be used to directly engage and transmit vibratory, usually ultrasonic, energy into the stenotic material in order to mechanically disrupt the material to open the associated blood vessel lumen. The catheters of the present invention will include vibrational transducers which are configured to vibrate in a direction normal to the plane of the transducer. In particular, the transducers will usually be bending plate transducers which are configured to bend about an axis which is normal to a plane of the transducer. Such bending plate transducers may have a variety of conventional structures, as will be described in more detail below in connection with FIGS. 3–6.

The catheters of the present invention will comprise a catheter body having a proximal end and a distal end. The catheter body will have dimensions and physical characteristics selected for the particular use. For vascular applications, the length of the catheter body will typically be from 50 cm to 200 cm, usually being from 75 cm to 150 cm, and the diameter will be from 1 mm to 5 mm, usually being from 2 mm to 4 mm. The diameter of the catheter body may vary over its length, and different portions of the length may be formed from different materials. In the exemplary embodiment, the catheter body will comprise a single extrusion typically having at least one lumen therethrough for providing guidewire access, drug infusion access, inflation medium access, or the like. Often, the catheter body may include multiple, separate lumens for balloon inflation, delivering therapeutic agent(s), routing electrical wires for connection to the ultrasonic transducer, or other purposes.

The catheter body may be composed of conventional materials and optionally be reinforced over all or a portion of its length. Conventional materials for the catheter body include synthetic and natural polymers, usually being thermoplastics, such as nylon, polyurethane, polyethyleneterephthalate (PET), polyvinylchloride (PVC), polyethylene, and the like. Such material may be conveniently extruded into tubular shapes useful for forming the catheter bodies of the present invention. Reinforcement materials may be introduced during the extrusion process or subsequent to extrusion by thermal processes, such as partial melting. Conventional reinforcement materials include wire and ribbon braids, wire meshes, wire coils, helical ribbons, and the like.

When employed with a guidewire for placement within the vasculature, the catheter body may have an "over-the-wire" design or a "rapid exchange" design. In the former case, the guidewire lumen will extend substantially through the entire length of the catheter body. In the latter case, the guidewire lumen will terminate in a proximal guidewire port located relatively near the distal end of the catheter body, usually within 50 cm, more usually within 30 cm, and often within 25 cm or less. Usually, a proximal housing will be secured to the proximal end of the catheter body, where the housing includes a guidewire port, a therapeutic agent infusion port, an electrical connector, and the like.

Figure 2:
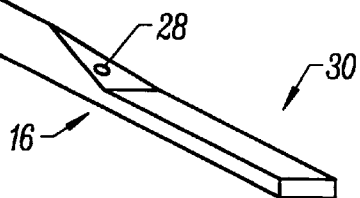
FIG. 2 is a detailed view of the distal end of the catheter of FIG. 1, with portions broken away.
Figure 2:
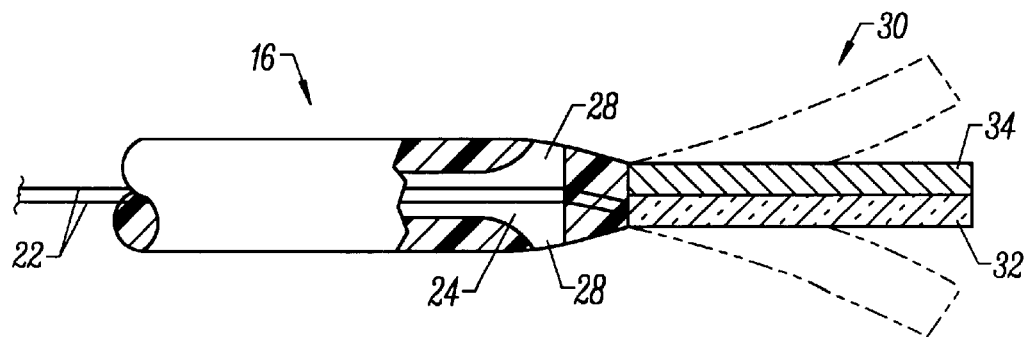

Referring to FIGS. 1 and 2, a catheter 10 comprises a catheter body 12 having the dimensions and characteristics described generally above. The catheter body has a proximal end 14, a distal end 16, and a proximal hub 18 attached to its proximal end. A connecting cable 20 enters the catheter 10 through the hub 18 and provides for external connection to wires 22, which in turn are connected to the vibrational transducer assembly 30, as described in more detail below. Catheter body 12 has a lumen 24 extending from an infusion tube 26 at its proximal end to a pair of infusion ports 28 at its distal end adjacent to the vibrational transducer 30. The infusion tube provides for connection to an external fluid source, such as a drug solution or other infusate which can be delivered through the catheter.

The vibrational transducer assembly 30, as illustrated in FIG. 2, comprises an active layer 32 laminated to an inactive layer 34. The active layer 32 typically comprises a piezoelectric material which can be electrically excited to oscillate in an axially direction. Such axial oscillation will cause bending of the assembly about a transverse axis, i.e. an axis which is normal to the cross-sectional view shown in FIG. 2. Thus, the transducer 30 will oscillate between positions as shown in broken line in FIG. 2.

The vibrational transducer 30 will be in the form of a plate, typically having a length in the range from 2 mm to 12 mm, preferably from 4 mm to 8 mm, a width in the range from 1 mm to 4 mm, preferably from 2 mm to 3 mm, and a thickness (extending across the two layers 32 and 34) in the range from 0.05 mm to 1 mm, preferably from 0.1 mm to 0.4 mm. Such transducers are referred to herein as "bending plate transducers," and may comprise conventional bimorph, unimorph, and other transducer structures. The structure shown in FIG. 2 is a bimorph structure where the active piezoelectric layer 32 will have electrode surfaces formed on opposed faces thereof. One face will be between the layers 32 and 34, and the other face will be on the opposite surface, i.e. on the top of the structure shown in FIG. 2. An alternating drive current can be applied to the electrodes through connector cable 20 and wires 22, typically having a voltage in the range from 10 volts to 200 volts, a current in the range from 0.01 mA to 5 mA, and a frequency in the range from 1 kHz to 40 kHz, usually from 2 kHz to 30 kHz. While the application of such current will cause expansion of the piezoelectric material of layer 32 in all directions, such expansions will be proportional to the depth of material in a particular direction. Thus, the major expansion will be along the axial length of the layer 32, preferentially causing bending as shown in broken line.

Figure 3:
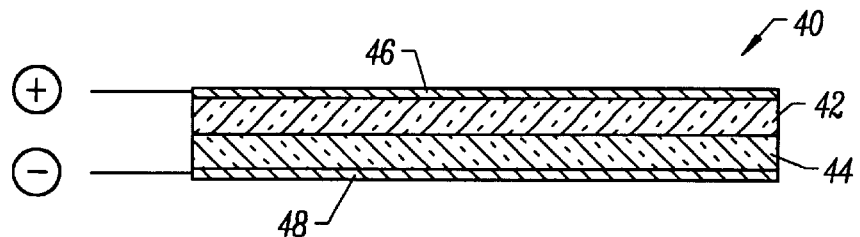
FIGS. 3–6 illustrates exemplary transducer constructions which may be utilized in the catheters of the present invention.
Figure 4:
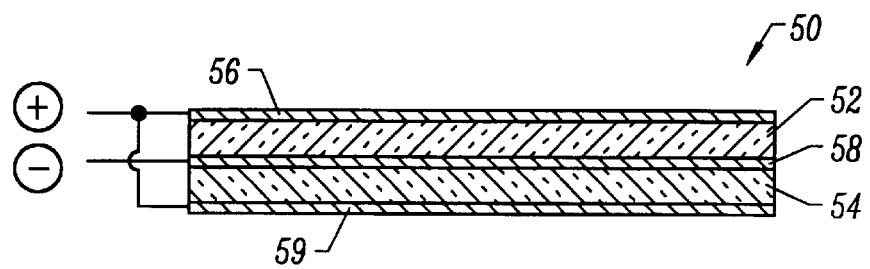

A variety of other suitable transducer structures will also be available for providing the bending plate transducers of the present invention. A bimorph transducer 40 comprising a pair of piezoelectric layers 42 and 44 is illustrated in FIG. 3. The piezoelectric materials have the opposite polarity, and are driven by electrode surfaces of 46 and 48 disposed on a opposed surfaces of each of the layers 42 and 44. The drive current described above will bend the transducer structure in the desired vibrational pattern.

An alternative bimorph transducer 50 comprises piezoelectric layers 52 and 54 having the same polarity. The transducer 50 is driven using three electrode surfaces 56, 58, and 59, which are driven with the same polarity at the outer surfaces (56 and 59), and the opposite polarity at the intermediate surface 58. This transducer structure is commonly referred to as a parallel bimorph with a center tap.

Figure 5:
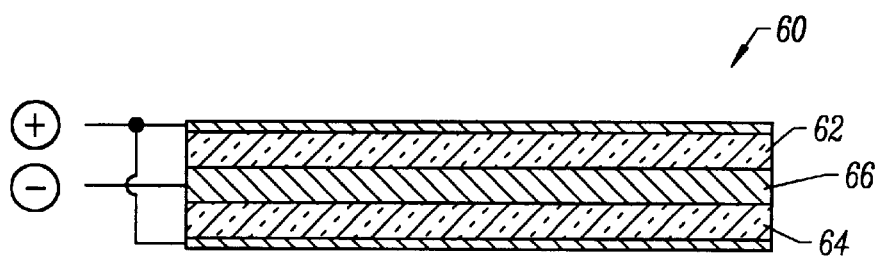

Referring now to FIG. 5 a tri-layer parallel bimorph assembly comprises piezoelectric layers 62 and 64 having the same polarity with a metal shim 66 therebetween. Driving of the transducer 60 is similar to that described in connection with transducer 50, with the metal shim acting as the center electrode. The shim 66, however, acts as an inactive layer, causing the transducer to which contributes to the structural strength of the assembly and permits greater displacements.

Figure 6:
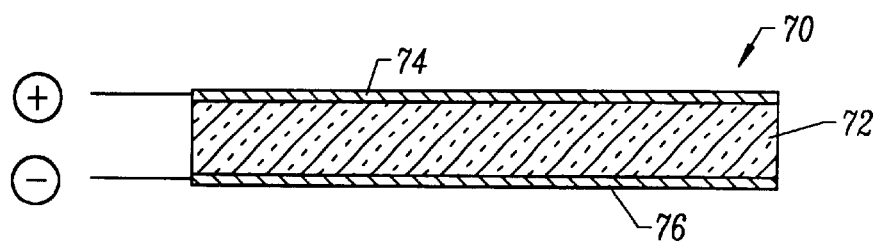

A variation of the single ceramic bimorph of FIG. 6 would further laminate the layer of ceramic 72 to a thin layer of metal. In this case, the metal layer remains inert and longitudinal expansions and contractions of the ceramic result in lateral displacements of the tip.

Referring now to FIG. 6, a unilaminar transducer 70 comprising a single layer 72 of piezoelectric material is driven by electrode surfaces 74 and 76. The piezoelectric layer 72 is internally biased (compressively stressed) and impregnated with ions to permit bi-directional actuation. Such structures are particularly convenient for use in the catheters of the present invention since they are compact, reliable, and provide relatively large displacements. Such transducers are commercially available from Aura Ceramics, Inc., Minneapolis, Minn.

Figure 7:
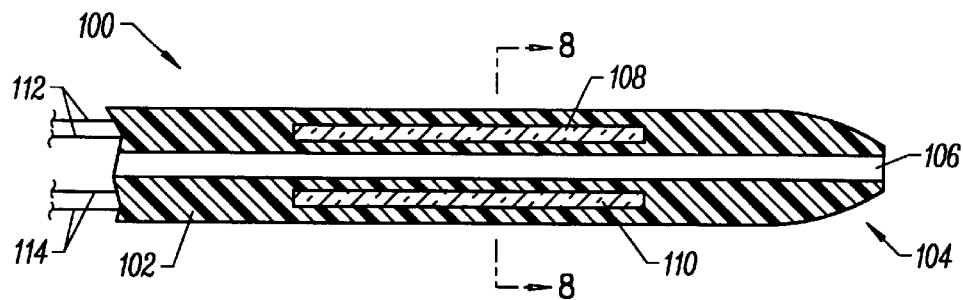
FIG. 7 is a cross-sectional view of the distal end of another catheter constructed in accordance with the principles of the present invention, having a pair of vibrational transducers embedded within the catheter body.
Figure 8:
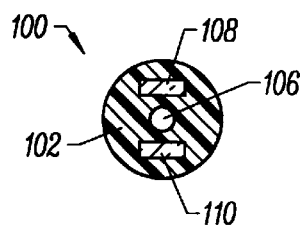
FIG. 8 is a cross-sectional view taken along line 8—8 of FIG. 7.

Referring now to FIGS. 7 and 8, a catheter 100 comprises a catheter body 102 having a proximal end (not shown), a distal end 104, and a lumen 106 extending between the proximal and distal ends. A pair of bending plate transducers 108 and 110 are disposed on opposite sides of the lumen 106 within the catheter body, as best observed in FIG. 8. Wires 112 and 114 are connected to the transducers 108 and 110, respectively, and permit driving of the transducers in the manner described above. The transducers 108 and 110 may take any of the forms described previously in connection with FIGS. 1–6. Provision of the transducers 108 and 110 within the catheter body will cause the catheter body to vibrate in a lateral manner. As the transducers 108 and 110 are damped along their lengths, they will not bend in the free manner of a cantilever transducer of the type shown in FIGS. 1 and 2. The catheter body 102 itself will act to transfer energy into a fluid environment or tissue structure surrounding the distal end of the catheter. Lumen 106 can be used for introducing the catheter over a guidewire and/or introducing a drug solution or other infusate to the region being treated.

Figure 9:
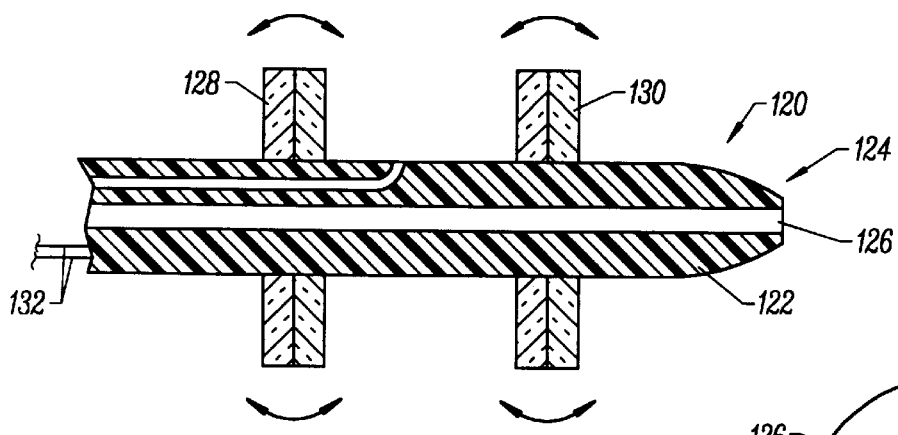
FIG. 9 is a cross-sectional view of the distal end of another catheter constructed in accordance with the principles of the present invention, having a pair of axially spaced-apart, transversely oriented annular transducers thereon.
Figure 10:
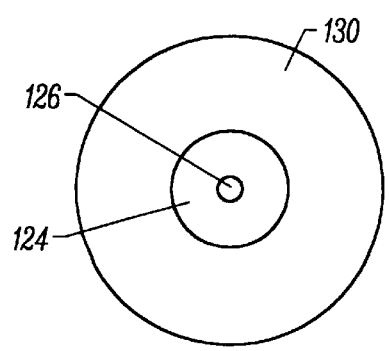
FIG. 10 is an end view of the catheter of FIG. 9.

Referring now to FIGS. 9 and 10, a catheter 120 comprising a catheter body 122 having a proximal end (not shown), a distal end 124, and a lumen 126 therethrough is illustrated. A pair of disk-like bending plate transducers 128 and 130 are axially spaced apart near the distal end of the catheter body 122. Wires 132 are provided for driving the transducers 128 and 130. While only two wires 132 are shown, it will be appreciated that additional wires may be provided for each of the transducers and/or to drive the transducers out of phase, if desired. The transducers 128 and 130 may have any of the layered structures described above in connection with FIGS. 1–6, and will be formed into an annular disk so that they can be mounted about the external periphery of the catheter body 122. The transducers will thus vibrate in the directions shown by the arrows, with the vibration being greatest at the free periphery of the transducers. Thus, the transducer operation is in many ways analogous to that described for the cantilever beam configuration of FIGS. 1 and 2. Instead of a lateral pressure wave, of course, the transducers 128 and 130 will produce an axial pressure wave which is imparted into the fluid environment surrounding the catheter 120.

Figure 11:
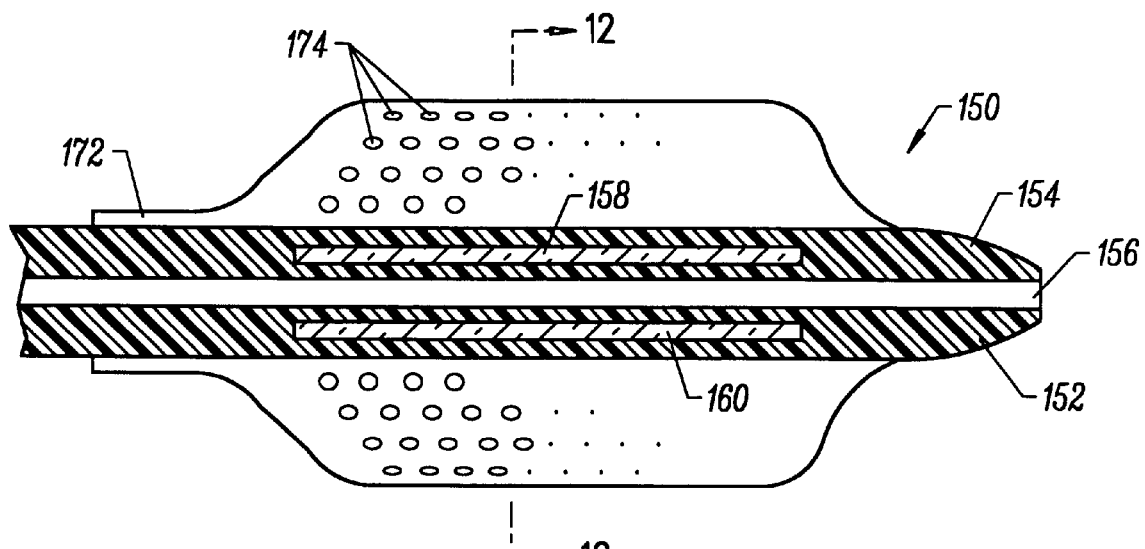
FIG. 11 is a cross-sectional view of the distal end of yet another catheter constructed in accordance with the principles of the present invention, having a balloon surrounding four symmetrically disposed, embedded vibrational transducers.
Figure 12:
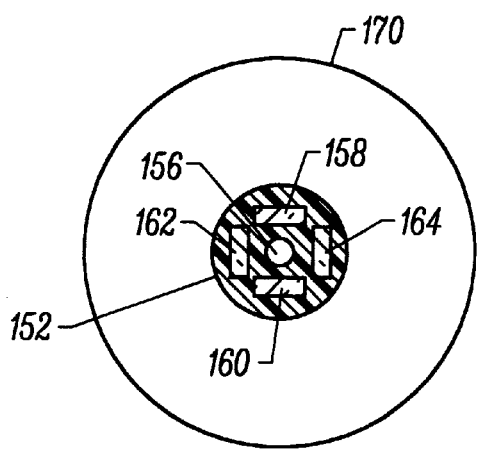
FIG. 12 is a cross-sectional view taken along line 12—12 of FIG. 11.

Referring now to FIGS. 11 and 12, a catheter 150 comprises a catheter body 152 having a proximal end (not shown) and a distal end 154. A lumen 156 extends from the proximal end to the distal end, and four transducers 158, 160, 162 and 164, are disposed symmetrically about the lumen 156 and embedded within the catheter body 152, as best observed in FIG. 12. The transducers may comprise any of the transducer structures described above, and can be driven in a synchronous or nonsynchronous manner.

An inflatable balloon 170 is disposed about the distal end of the catheter 150 generally over the transducers 158–164. The balloon 170 may be inflated through a coaxial lumen 172 or another lumen formed in the catheter body 152. By inflating the balloon 170 with an incompressible fluid, typically saline, vibrational energy produced by electrically driving the transducers 158–164 can be transmitted through the balloon and into an adjacent lumenal wall and/or occluding material within a body lumen. The balloon can be inflated at a relatively low pressure, e.g. below 1 atmosphere, or can be inflated to much higher pressures associated with angioplasty treatment, typically in the range from 5 atmospheres to 20 atmospheres. In some cases, it may be desirable to employ a perforate balloon structure 172, such as described in U.S. Pat. No. 5,611,755, the full disclosure of which is incorporated herein by reference, in order to release a drug solution or other therapeutic agent through the balloon and to the vascular wall. The introduction of vibrational energy into the infusate can enhance intramural penetration of the drug into the vascular or other lumenal wall. Exemplary perforations 174 are illustrated in FIG. 11.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A catheter comprising:

a catheter body having a proximal end and a distal end; and a bending plate transducer attached to the catheter body near the distal end thereof, the transducer arranged to vibrationally flex about an axis within a plane of the transducer.

2. A catheter as in claim 1, wherein at least a portion of the transducer projects distally from the distal end of the catheter body.

3. A catheter as in claim 1, wherein the transducer is disposed within the catheter body.

4. A catheter as in claim 1, wherein the transducer comprises at least one active layer which oscillates axially when energized and at least one opposed layer which constrains or oscillates non-synchronously relative to the active layer, wherein the relative axial displacement of the active and opposed layers causes transverse flexing of the transducer.

5. A catheter as in claim 4, wherein the active layer comprises a piezoelectric material.

6. A catheter as in claim 5, wherein the opposed layer comprises an inactive material laminated to a face of the active layer to constrain axial displacement and cause transverse bending.

7. A catheter as in claim 6, wherein the inactive material is a metal sheet laminated to the face of the active layer.

8. A catheter as in claim 7, wherein the piezoelectric layer has a thickness in the range from 0.1 mm to 1 mm and the metal sheet has a thickness in the range from 0.05 mm to 0.5 mm.

9. A catheter as in claim 8, wherein the transducer further comprises a second active layer composed of a piezoelectric material laminated to an opposite face of the inactive metal layer, said second active piezoelectric layer having a thickness in the range from 0.1 mm to 1 mm.

10. A catheter as in claim 4, wherein the opposed layer comprises an active piezoelectric material.

11. A catheter as in claim 10, wherein the piezoelectric material of the active layer has a polarity opposite to that of the piezoelectric material of the opposed layer, wherein the active layer and opposed layer are energized in phase.

12. A catheter as in claim 10, wherein the piezoelectric material of the active layer has a polarity which is the same as that of the piezoelectric material of the opposed layer, wherein the active layer and opposed layer are energized out-of-phase.

13. A catheter as in claim 1, wherein the transducer comprises a layer of ion impregnated piezoelectric ceramic material.

14. A catheter as in claim 1, further comprising a balloon disposed near the distal end of the catheter body over at least a portion of the bending plate transducer.

15. A catheter as in claim 1, further comprising at least a second bending plate transducer disposed near the distal end of the catheter body.

16. A catheter as in claim 1, further comprising means for delivering a fluid agent from the proximal end of the catheter body to a region near the bending plate transducer at the distal end thereof.

17. A catheter as in claim 1, wherein the bending plate transducer is an annular disk disposed transversely to the axis of the catheter body.

18. A method for intralumenal delivery of vibrational energy to a body lumen, said method comprising:

providing a catheter having a bending plate transducer near a distal end thereof;

positioning the catheter with a body lumen so that the transducer lies adjacent a target site within the body lumen; and energizing the transducer to vibrationally flex the transducer about an axis within the plane of the transducer.

19. A method as in claim 18, wherein the transducer vibrates at a frequency in the range from 1 kHz to 40 kHz.

20. A method as in claim 19, wherein the transducer vibrates with an amplitude of at least 5 $\mu$m at its distal tip when energized at the target site.

21. A method as in claim 18, wherein the body lumen is a blood vessel and the target site is a stenosed region.

22. A method as in claim 21, wherein the stenosed region has previously been treated by angioplasty.

23. A method as in claim 18, further comprising releasing a therapeutic agent at the target site.

24. A method as in claim 23, wherein the therapeutic agent is released prior to energizing the transducer.

25. A method as in claim 23, wherein the therapeutic agent is released while energizing the transducer.

26. A method as in claim 18, further comprising inflating a balloon around the transducer within the body lumen while the transducer is being energized.

* * * * *